United States Patent
Ng et al.

(10) Patent No.: US 9,676,164 B2
(45) Date of Patent: Jun. 13, 2017

(54) EXTENSIBLE SHEET MATERIAL WITH VISUAL STRETCH INDICATOR

(75) Inventors: Wing-Chak Ng, Roswell, GA (US); Jose Augusto Vidal de Siqueira, Roswell, GA (US); Lawrence H. Sawyer, Neenah, WI (US); Charles W. Colman, Marietta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1399 days.

(21) Appl. No.: 13/185,151

(22) Filed: Jul. 18, 2011

(65) Prior Publication Data

US 2013/0022794 A1    Jan. 24, 2013

(51) Int. Cl.
| | | |
|---|---|---|
| B32B 3/00 | (2006.01) | |
| B32B 3/26 | (2006.01) | |
| B32B 5/02 | (2006.01) | |
| B32B 5/18 | (2006.01) | |
| B32B 27/30 | (2006.01) | |
| B32B 27/32 | (2006.01) | |
| B32B 3/18 | (2006.01) | |
| B32B 5/14 | (2006.01) | |
| A61F 13/49 | (2006.01) | |
| A61F 13/84 | (2006.01) | |

(52) U.S. Cl.
CPC .......... *B32B 3/266* (2013.01); *A61F 13/4902* (2013.01); *A61F 13/84* (2013.01); *B32B 3/18* (2013.01); *B32B 5/022* (2013.01); *B32B 5/142* (2013.01); *B32B 5/18* (2013.01); *B32B 27/302* (2013.01); *B32B 27/32* (2013.01); *A61F 2013/8497* (2013.01); *B32B 2307/402* (2013.01); *B32B 2307/51* (2013.01); *B32B 2307/728* (2013.01); *B32B 2555/02* (2013.01); *Y10T 428/24802* (2015.01)

(58) Field of Classification Search
None
See application file for complete search history.

(56) References Cited

U.S. PATENT DOCUMENTS

| | | | |
|---|---|---|---|
| 1,603,813 | A | 10/1926 | Jacob |
| 3,321,804 | A | 5/1967 | Breidt, Jr. et al. |
| 3,405,425 | A | 10/1968 | Buckley et al. |
| 3,449,186 | A | 6/1969 | Rano |
| 3,485,912 | A | 12/1969 | Schrenk et al. |
| 3,555,128 | A | 1/1971 | Schrenk |
| 3,565,985 | A | 2/1971 | Schrenk et al. |

(Continued)

FOREIGN PATENT DOCUMENTS

| | | |
|---|---|---|
| DE | 198 06 452 A1 | 8/1999 |
| EP | 0 018 020 A1 | 10/1980 |

(Continued)

*Primary Examiner* — Ian Rummel

(57) ABSTRACT

As described herein, an extensible sheet material includes a first and a second zone that is separate from the first zone. The first zone exposes a first color or pattern when the extensible sheet material is stretched beyond a first percentage. The second zone exposes a second color or pattern when the extensible sheet material is stretched beyond a second percentage greater than the first percentage. Absorbent articles that include the extensible sheet material are capable of indicating to a wearer when the extensible sheet material has been stretched too little, too much, or just the right amount.

18 Claims, 7 Drawing Sheets

(56) References Cited

U.S. PATENT DOCUMENTS

| | | | |
|---|---|---|---|
| 3,687,589 A | 8/1972 | Schrenk | |
| 3,738,790 A | 6/1973 | Violette et al. | |
| 3,756,758 A | 9/1973 | Prall | |
| 3,764,450 A * | 10/1973 | Tesch | 428/136 |
| 3,800,796 A | 4/1974 | Jacob | |
| 3,807,918 A | 4/1974 | Chill et al. | |
| 3,989,867 A | 11/1976 | Sisson | |
| 4,050,972 A | 9/1977 | Cardinal, Jr. | |
| 4,283,168 A | 8/1981 | Miller et al. | |
| 4,435,141 A | 3/1984 | Weisner et al. | |
| 4,521,359 A | 6/1985 | Tsien | |
| 4,533,510 A | 8/1985 | Nissel | |
| 4,662,875 A | 5/1987 | Hirotsu et al. | |
| 4,731,004 A | 3/1988 | Wenz, Jr. | |
| 4,777,073 A | 10/1988 | Sheth | |
| 4,781,962 A | 11/1988 | Zamarripa et al. | |
| 4,883,480 A | 11/1989 | Huffman et al. | |
| 5,045,264 A | 9/1991 | Kirksey | |
| 5,057,097 A | 10/1991 | Gesp | |
| 5,120,484 A | 6/1992 | Cloeren | |
| 5,223,276 A | 6/1993 | Djordjevic et al. | |
| 5,501,679 A | 3/1996 | Krueger et al. | |
| 5,567,376 A | 10/1996 | Turi et al. | |
| 5,620,780 A | 4/1997 | Krueger et al. | |
| 5,635,276 A | 6/1997 | Biagioli et al. | |
| 5,766,389 A | 6/1998 | Brandon et al. | |
| 5,800,903 A | 9/1998 | Wood et al. | |
| 5,807,368 A | 9/1998 | Helmer | |
| 5,843,554 A | 12/1998 | Katz | |
| 5,855,999 A | 1/1999 | McCormack | |
| 5,885,908 A | 3/1999 | Jaeger et al. | |
| 5,968,029 A | 10/1999 | Chappell et al. | |
| 5,993,432 A | 11/1999 | Lodge et al. | |
| 6,045,543 A | 4/2000 | Pozniak et al. | |
| 6,100,208 A | 8/2000 | Brown et al. | |
| 6,159,584 A | 12/2000 | Eaton et al. | |
| 6,221,483 B1 | 4/2001 | Hilston et al. | |
| 6,245,401 B1 | 6/2001 | Ying et al. | |
| 6,255,236 B1 | 7/2001 | Cree et al. | |
| 6,277,479 B1 | 8/2001 | Campbell et al. | |
| 6,403,505 B1 | 6/2002 | Groitzsch et al. | |
| 6,409,494 B1 | 6/2002 | Voss | |
| 6,432,074 B1 | 8/2002 | Ager et al. | |
| 6,472,084 B1 | 10/2002 | Middlesworth et al. | |
| 6,531,207 B1 | 3/2003 | Eaton et al. | |
| 6,572,575 B1 | 6/2003 | Shimada et al. | |
| 6,626,206 B1 | 9/2003 | Ulcei et al. | |
| 6,627,791 B1 | 9/2003 | Veglio et al. | |
| 6,669,887 B2 | 12/2003 | Hilston et al. | |
| 6,692,477 B2 | 2/2004 | Gibbs | |
| 6,729,867 B2 | 5/2004 | Peter et al. | |
| 6,740,071 B2 | 5/2004 | Gibbs | |
| 6,780,272 B2 | 8/2004 | Wood | |
| 6,916,969 B1 | 7/2005 | Helmfridsson et al. | |
| 6,927,315 B1 | 8/2005 | Heinecke et al. | |
| 6,942,651 B2 | 9/2005 | Gibbs | |
| 6,949,283 B2 | 9/2005 | Kollaja et al. | |
| 7,014,631 B2 | 3/2006 | Jackson et al. | |
| 7,037,300 B2 | 5/2006 | Kling | |
| 7,039,990 B2 | 5/2006 | Gorman et al. | |
| 7,048,013 B2 | 5/2006 | Shannon | |
| 7,102,054 B1 | 9/2006 | Cree et al. | |
| 7,316,675 B2 | 1/2008 | Soga et al. | |
| 7,347,845 B2 | 3/2008 | Zajaczkowski | |
| 7,462,172 B2 | 12/2008 | Wright et al. | |
| 7,534,481 B2 | 5/2009 | Seth et al. | |
| 7,569,040 B2 | 8/2009 | Nakahata et al. | |
| 7,589,249 B2 | 9/2009 | Gubernick et al. | |
| 7,674,949 B2 | 3/2010 | Wahlstrom et al. | |
| 7,704,589 B2 | 4/2010 | Olson et al. | |
| 7,744,579 B2 | 6/2010 | Langdon et al. | |
| 7,799,162 B2 | 9/2010 | Wood et al. | |
| 7,870,651 B2 | 1/2011 | Middlesworth et al. | |
| 7,897,081 B2 | 3/2011 | Ausen et al. | |
| 7,943,537 B2 | 5/2011 | Vincent et al. | |
| 8,016,807 B2 | 9/2011 | Kline et al. | |
| 8,067,063 B2 | 11/2011 | Desai et al. | |
| 8,088,116 B2 | 1/2012 | Kline et al. | |
| 8,182,456 B2 | 5/2012 | Autran et al. | |
| 8,188,333 B2 | 5/2012 | Matsuoka et al. | |
| 8,198,200 B2 | 6/2012 | Autran et al. | |
| 8,211,078 B2 | 7/2012 | Noel | |
| 8,227,660 B2 | 7/2012 | Hara et al. | |
| 8,357,135 B2 | 1/2013 | De Dier et al. | |
| 8,460,588 B2 | 6/2013 | Lake et al. | |
| 2001/0037851 A1 | 11/2001 | Mortellite et al. | |
| 2003/0125687 A1 | 7/2003 | Gubernick et al. | |
| 2003/0136497 A1 | 7/2003 | Hamulski et al. | |
| 2003/0173015 A1 | 9/2003 | Hamulski et al. | |
| 2003/0194936 A1 | 10/2003 | Jackson et al. | |
| 2004/0013850 A1 | 1/2004 | Kling | |
| 2004/0044324 A1 | 3/2004 | Swenson et al. | |
| 2004/0122396 A1 | 6/2004 | Maldonado et al. | |
| 2005/0095943 A1 | 5/2005 | Griffin et al. | |
| 2005/0148971 A1 | 7/2005 | Kuroda et al. | |
| 2005/0215972 A1 | 9/2005 | Roe et al. | |
| 2006/0047259 A1 | 3/2006 | Erdman et al. | |
| 2006/0068168 A1 * | 3/2006 | Olson et al. | 428/152 |
| 2006/0083907 A1 | 4/2006 | Bech et al. | |
| 2006/0137079 A1 | 6/2006 | Goodrich et al. | |
| 2006/0147686 A1 | 7/2006 | Ausen et al. | |
| 2006/0246802 A1 * | 11/2006 | Hughes et al. | 442/327 |
| 2006/0288547 A1 | 12/2006 | Jackson | |
| 2007/0130732 A1 | 6/2007 | Matsumura et al. | |
| 2007/0141352 A1 | 6/2007 | Calhoun et al. | |
| 2007/0142798 A1 | 6/2007 | Goodlander et al. | |
| 2007/0250023 A1 | 10/2007 | Strannemalm | |
| 2008/0070007 A1 | 3/2008 | Vincent et al. | |
| 2008/0095978 A1 | 4/2008 | Siqueira et al. | |
| 2008/0099951 A1 | 5/2008 | Batch et al. | |
| 2008/0108267 A1 | 5/2008 | Baldauf et al. | |
| 2008/0113153 A1 | 5/2008 | Tiozzo | |
| 2008/0138598 A1 | 6/2008 | Michel et al. | |
| 2008/0233418 A1 * | 9/2008 | Krueger | 428/523 |
| 2009/0247980 A1 | 10/2009 | Aiken | |
| 2009/0312736 A1 | 12/2009 | Schroer, Jr. et al. | |
| 2010/0324517 A1 | 12/2010 | Lenhult et al. | |
| 2011/0160691 A1 | 6/2011 | Ng et al. | |
| 2011/0206943 A1 | 8/2011 | Willis et al. | |
| 2012/0172826 A1 | 7/2012 | Ng et al. | |
| 2013/0022794 A1 | 1/2013 | Ng et al. | |

FOREIGN PATENT DOCUMENTS

| | | |
|---|---|---|
| EP | 0 707 938 A2 | 4/1996 |
| EP | 0 756 855 A1 | 2/1997 |
| EP | 0 792 733 A1 | 9/1997 |
| EP | 1 078 620 A2 | 2/2001 |
| EP | 0 834 387 B1 | 7/2003 |
| EP | 1 591 091 A2 | 11/2005 |
| GB | 1 311 085 A | 3/1973 |
| GB | 2 267 024 A | 11/1993 |
| JP | 09-174646 A | 7/1997 |
| JP | 2001-328180 A | 11/2001 |
| JP | 2006-159537 A | 6/2006 |
| KR | 0137121 Y1 | 3/1999 |
| KR | 10-2005-0090403 A | 9/2005 |
| KR | 10-2006-0094537 A | 8/2006 |
| WO | WO 92/01759 A1 | 2/1992 |
| WO | WO 01/21126 A1 | 3/2001 |
| WO | WO 01/32403 A1 | 5/2001 |
| WO | WO 03/034966 A1 | 5/2003 |
| WO | WO 2005/037159 A1 | 4/2005 |
| WO | WO 2005/053588 A1 | 6/2005 |
| WO | WO 2006/065175 A1 | 6/2006 |
| WO | WO 2008/099438 A2 | 10/2008 |
| WO | WO 2009/005413 A1 | 1/2009 |
| WO | WO 2009/157835 A1 | 12/2009 |
| WO | WO 2011/104014 A1 | 9/2011 |

* cited by examiner

EXTENSIBLE SHEET MATERIAL WITH VISUAL STRETCH INDICATOR

BACKGROUND OF THE INVENTION

Absorbent articles such as diapers, training pants, incontinence garments, swim pants, fitted briefs and the like conventionally include a liquid permeable body-facing liner, a liquid impermeable outer cover, and an absorbent core. The absorbent core is typically located in between the outer cover and the liner for taking in and retaining liquids (e.g., urine) exuded by the wearer.

In some of these absorbent articles, the articles contain various elastic materials to permit some expansion of the article when necessary and/or to provide a better fit on the wearer. For example, some absorbent articles have been made in the past containing waist elastic members that allow the waist of the article to expand and contract. Absorbent articles have also been made with side elastic members that allow the articles to expand around the hip of a wearer. The elastic components not only provide the article with some form-fitting properties but also allow the article to accommodate a range of sizes.

However, problems may occur if a caregiver does not extend the elastic components the proper amount when putting the article on the wearer. For example, extending the elastic components too little may result in a saggy product that does not have the proper tension to fit properly on the wearer's body. Alternatively, extending the elastic components too much may result in the product being too tight on the wearer's body, leading to chafing, red-marking, or other discomfort for the wearer. In addition, caregivers may not know when to use the next larger size of the articles as the wearers grow out of the fit range of the current size.

Therefore, a need exists for a garment that includes an indicator of when the elastic components have been stretched into the proper range. Specifically, a need exists for a garment that is capable of indicating to the user when the elastic components have not been stretched far enough once the garment is placed on the wearer. A need also exists for a garment that is capable of indicating when the elastic components have been stretched too far once placed on the wearer.

SUMMARY OF THE INVENTION

In general, the present invention is directed to an extensible sheet material with a built-in visual stretch indicator. Through the visual stretch indicator, absorbent articles that include the extensible sheet material with the visual stretch indicator are capable of indicating to a wearer when the extensible sheet material has been stretched too little, too much, or just the right amount.

For example, in one embodiment, an extensible sheet material includes a first and a second zone that is separate from the first zone. The first zone exposes a first color or pattern when the extensible sheet material is stretched beyond a first percentage. Further, the second zone exposes a second color or pattern when the extensible sheet material is stretched beyond a second percentage greater than the first percentage. In some embodiments the first percentage is from about 10 percent to about 50 percent. In some embodiments, the second percentage is from about 30% to about 150%. In further embodiments, the second color or pattern may substantially disappear upon retraction of the extensible sheet material to an extension less than the second percentage.

In one aspect, the ratio of a second zone extension force at 30% extension to a first zone extension force at 30% extension is from about 1.01 to about 5, optionally from about 1.5 to about 3. Alternatively, the ratio of the second zone extension force at 100% extension to the first zone extension force at 100% extension is from about 1.01 to about 5, optionally from about 1.5 to about 3.

In another aspect, the extensible sheet material may be elastic. In some embodiments, the extensible sheet material may include an elastic layer and at least one facing layer. In other embodiments the extensible sheet material may be a stretch-bonded laminate, neck bonded laminate, or neck stretch bonded laminate. In further embodiments, the at least one elastic layer may include first and second elastic layer zones corresponding to the first and second zones of the extensible sheet material, wherein the first elastic layer zone consists of a first elastic composition, and wherein the second elastic layer zone consists of a second elastic composition. Suitably, the first elastic composition may have a modulus lower than the modulus of the second elastic composition. In some embodiments, the first elastic composition may include predominantly a styrenic block copolymer, and the second elastic composition may include predominantly an elastic polyolefin. In other embodiments, the facing layer is selected from the group consisting of woven materials, nonwoven materials, films, foams, and laminates thereof.

In a further aspect, at least one facing layer includes first and second facing layer zones corresponding to the first and second zones of the extensible sheet material, wherein the first facing layer zone includes a first plurality of slits through which the first color or pattern is exposed when the extensible sheet material is stretched beyond the first percentage, and wherein the second facing layer zone includes a second plurality of slits through which the second color or pattern is exposed when the extensible sheet material is stretched beyond the second percentage. In some embodiments, the first plurality of slits may have a first slit length, and the second plurality of slits may have a second slit length, and the first slit length may be larger than the second slit length. In other embodiments, the first plurality of slits may have a first slit depth equal to or less than the thickness of the first facing layer zone, and the second plurality of slits may have a second slit depth less than the thickness of the second facing layer zone, and the first slit depth may be larger than the second slit depth. In a further embodiment, the first plurality of slits may have a first slit density, and the second plurality of slits have a second slit density, and the first slit density may be greater than the second slit density.

In an even further aspect, at least one facing layer comprises a foam or other material without slits wherein the at least one facing layer comprises first and second facing layer zones corresponding to the first and second zones of the extensible sheet material, wherein the first facing layer zone exposes the first color or pattern when the extensible sheet material is stretched beyond the first percentage, and wherein the second facing layer zone exposes the second color or pattern when the extensible sheet material is stretched beyond the second percentage.

In other aspects, the extensible sheet material may be used as a component of an absorbent product or garment.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
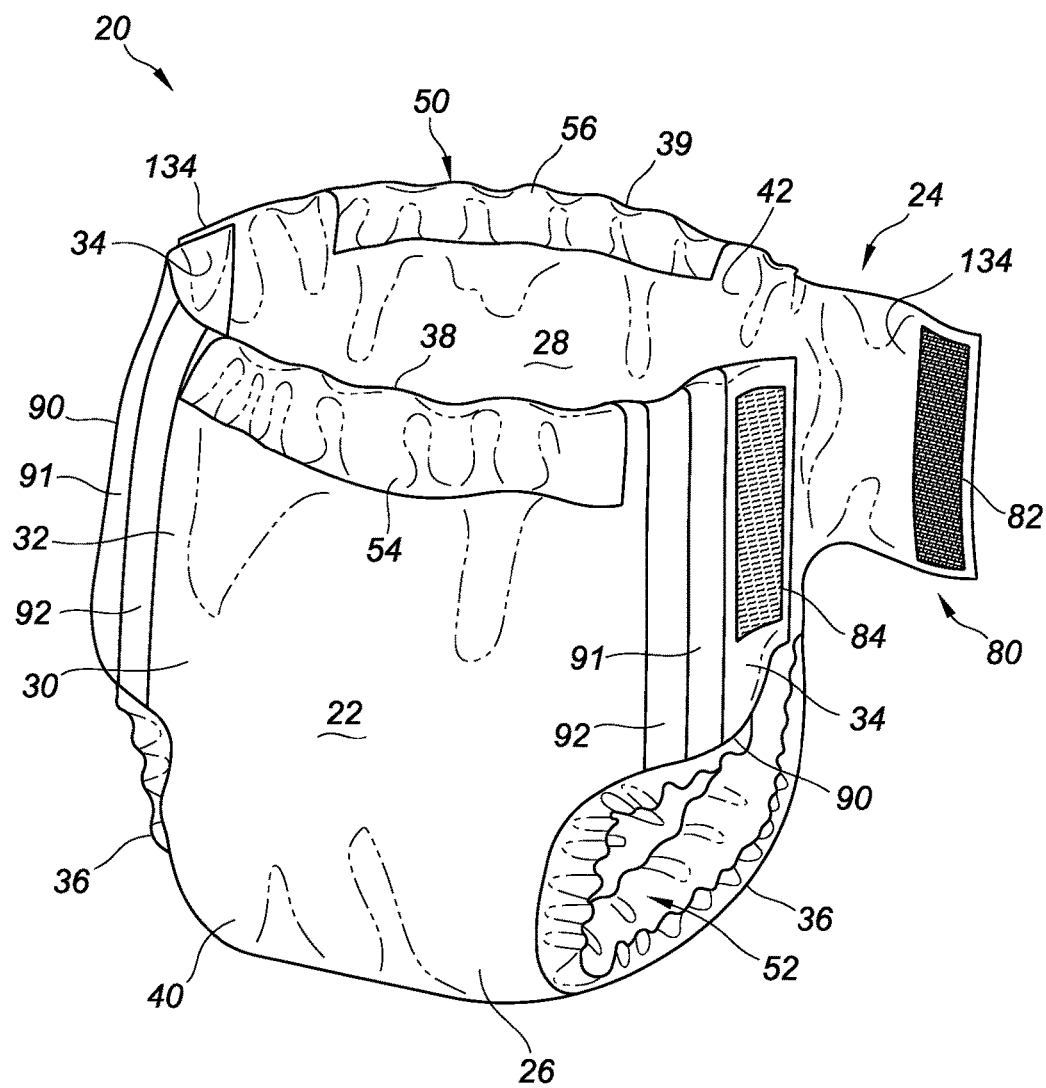
FIG. 1 is a perspective view of one embodiment of an absorbent article made in accordance with the present invention.

Repeat use of reference characters in the present specification and drawings is intended to represent the same or analogous features or elements of the present invention.

DEFINITIONS

As used herein, the "longitudinal direction" is a direction that extends from the front region of an absorbent article through a crotch region and to the back region.

As used herein, the "transverse direction" is the direction perpendicular to the longitudinal direction.

As used herein, the term "stretchable" refers to a material that may be stretchable and/or elastic (or elastomeric). That is, the material may be extended, deformed or the like, without breaking, and may or may not significantly retract after removal of an extending force.

As used herein, the term "extensible" refers to a material that is stretchable but is not elastic.

As used herein, the term "percent stretch" refers to the amount a material is stretched based on its original unstretched length. For example, a material that is stretched 100% is stretched until its length doubles in size.

As used herein, the term "stretch bonded laminate" refers to a composite material having at least two layers in which one layer is a gatherable layer and the other layer is an elastic layer.

As used herein, the term "neck bonded laminate" refers to a composite material having an elastic member that is bonded to a non-elastic member while the non-elastic member is extended in the machine direction creating a necked material that is elastic in the cross-direction.

DETAILED DESCRIPTION

It is to be understood by one of ordinary skill in the art that the present discussion is a description of exemplary embodiments only, and is not intended as limiting the broader aspects of the present invention.

In general, the present invention is directed to an absorbent article that includes an extensible component with a visual stretch indicator for indicating to the user whether the elastic component has been stretched by an appropriate amount. The absorbent article may be, for instance, a diaper, a toilet training pant, an adult incontinence garment, a swim pant, a fitted brief, or the like. The extensible component is constructed such that a first zone and a second zone expose first and second colors or patterns in response to different levels of stress and strain applied to them. For example, in one embodiment, the first zone may be configured to expose a first color or first pattern when the first zone is stretched beyond a certain first percentage indicating to the user that the elastic component has been stretched to an appropriate amount. Further, the second zone may be configured to expose a second color or second pattern when the second zone is stretched beyond a certain second percentage indicating to the user that the elastic component has been stretched beyond an appropriate amount. In this embodiment, the certain first percentage is less than the certain second percentage. The first percentage may suitably be from about 10 percent to about 50 percent. The second percentage may suitably be from about 30% to about 150%.

As will be described in more detail below, the manner in which the first and second zones expose a color or pattern can vary depending upon the particular application. In some embodiments, for instance, the extensible sheet material includes an elastic layer and at least one facing layer. For example, the extensible sheet material may be a stretch-bonded laminate, neck bonded laminate, or neck stretch bonded laminate.

In one embodiment, the ratio of the second zone extension force at 30% extension to the first zone extension force at 30% extension is from about 1.01 to about 5, more particularly from about 1.5 to about 3. In a further embodiment, the ratio of the second zone extension force at 100% extension to the first zone extension force at 100% extension is from about 1.01 to about 5, more particularly from about 1.5 to about 3.

In another embodiment, the at least one facing layer includes first and second facing layer zones corresponding to the first and second zones of the extensible sheet material. The first facing layer zone may include a first plurality of slits through which the first color or pattern is exposed when the extensible sheet material is stretched beyond the first percentage. The second facing layer zone includes a second plurality of slits through which the second color or pattern is exposed when the extensible sheet material is stretched beyond the second percentage. In one aspect, the first plurality of slits have a first slit length, and wherein the second plurality of slits have a second slit length, and further wherein the first slit length is larger than the second slit length. In another aspect, the first plurality of slits have a first slit depth equal to or less than the thickness of the first facing layer zone, and wherein the second plurality of slits have a second slit depth less than the thickness of the second facing layer zone, and further wherein the first slit depth is larger than the second slit depth. In a further aspect, the first plurality of slits have a first slit density (number of slits per unit area), and wherein the second plurality of slits have a second slit density, and further wherein the first slit density is greater than the second slit density.

In another embodiment, the at least one facing layer includes a foam or other material without slits wherein the at least one facing layer includes first and second facing layer zones corresponding to the first and second zones of the extensible sheet material. The first facing layer zone exposes the first color or pattern when the extensible sheet material is stretched beyond the first percentage. The second facing layer zone exposes the second color or pattern when the extensible sheet material is stretched beyond the second percentage.

In addition or instead of exposing a color, the first and second zones of the present invention can also be configured to expose a pattern when stretched. For example, when stretched, the first and/or second zones may expose linear lines, rows or columns, a checkerboard-like pattern, words, symbols, letters, phrases, and so forth.

Figure 6:
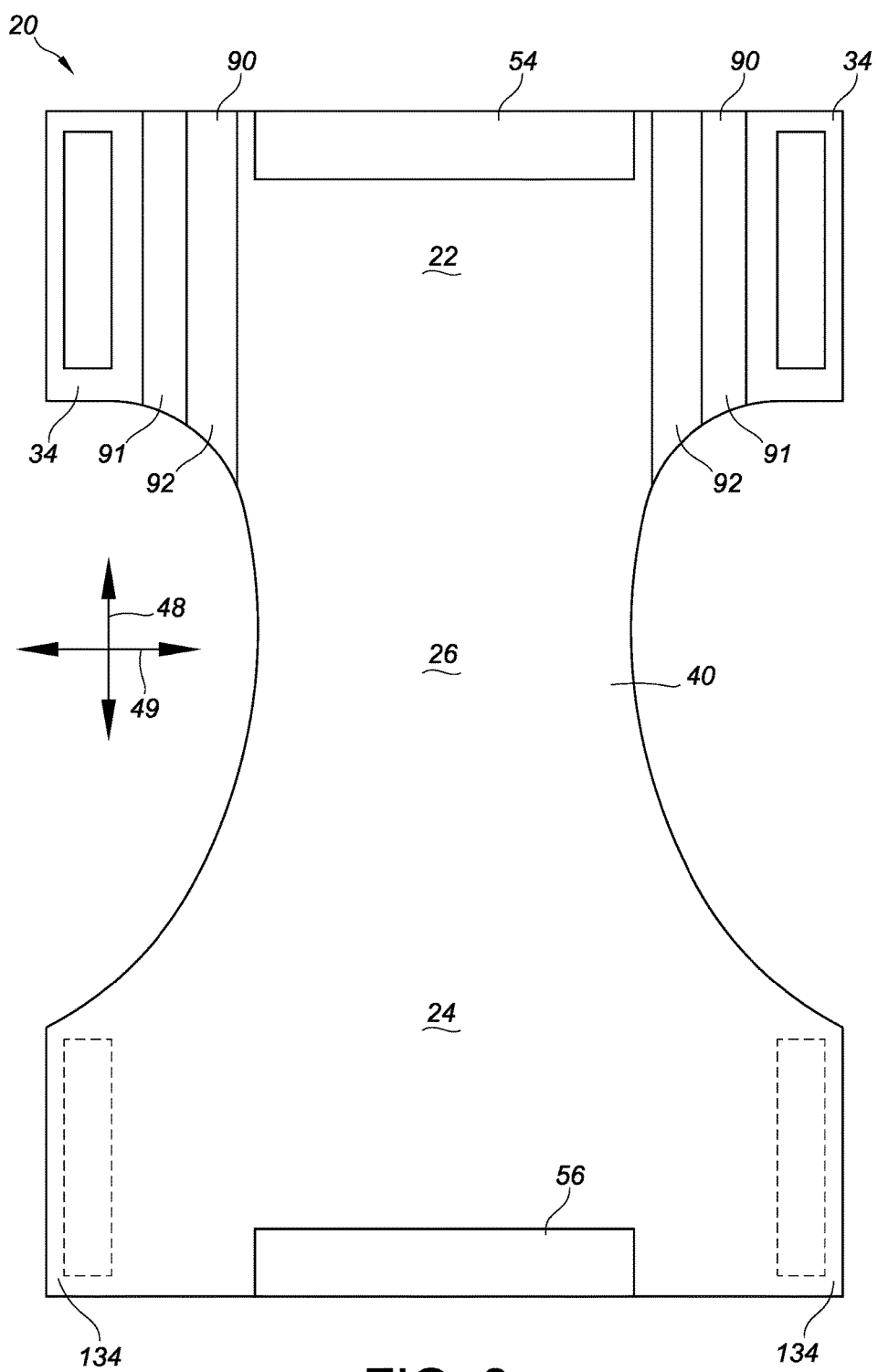
FIG. 6 is a plan view of the absorbent article illustrated in FIG. 1.
Figure 7:
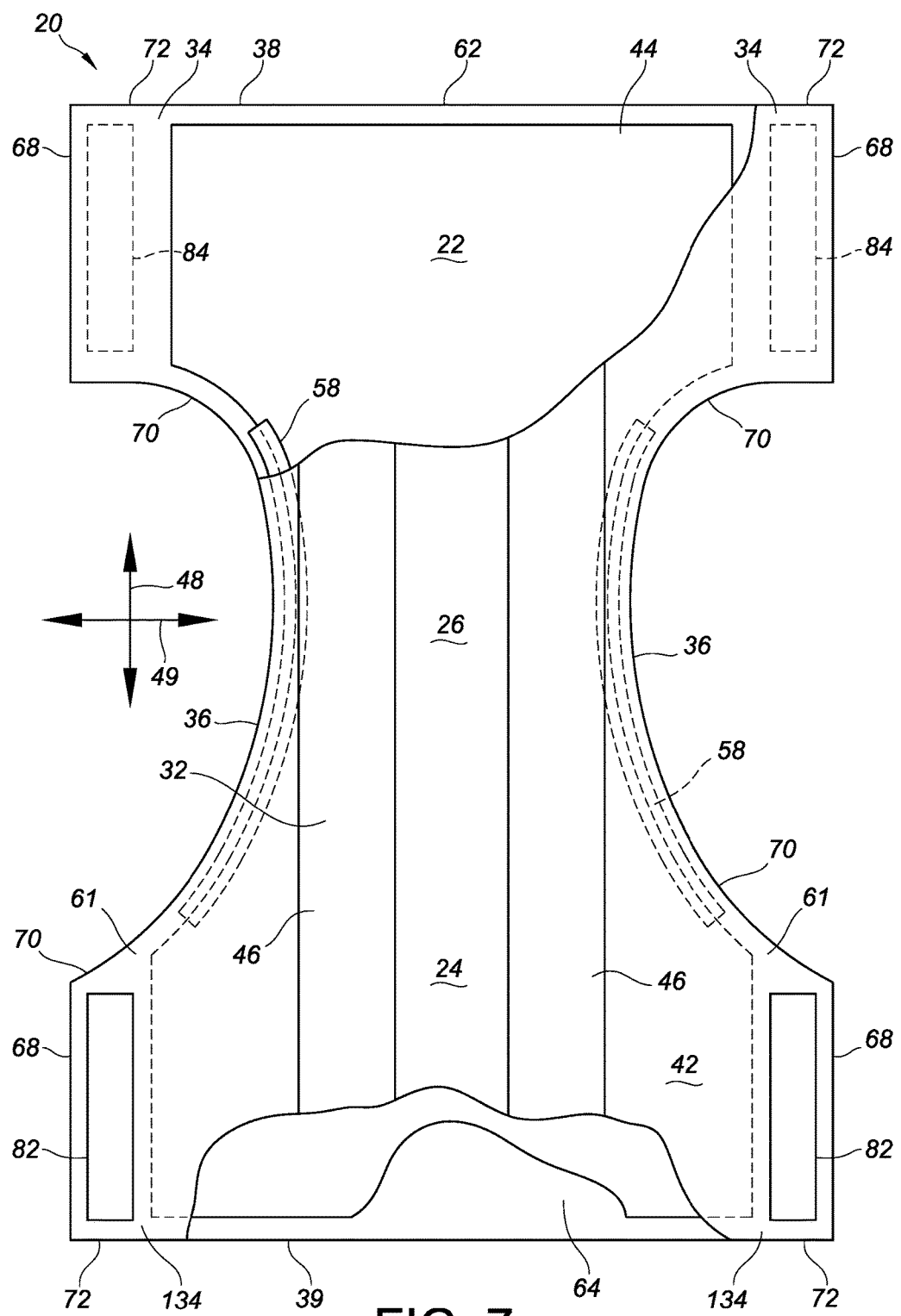
FIG. 7 is a plan view of the opposite side of the absorbent article illustrated in FIG. 6.

For exemplary purposes, a pair of training pants 20 is representatively illustrated in FIG. 1 in a partially fastened condition. The training pant 20 shown in FIG. 1 is also represented in FIGS. 6 and 7 in an opened and unfolded state. Specifically, FIG. 6 is a plan view illustrating the exterior side of the pants 20, while FIG. 7 illustrates the interior side of the pants 20. As shown in FIGS. 6 and 7, the pants 20 define a longitudinal direction 48 that extends from the front of the training pants when worn to the back of the training pants. Opposite to the longitudinal direction 48 is a lateral direction 49.

The pants 20 define a pair of longitudinal end regions, otherwise referred to herein as a front region 22 and a back region 24, and a center region, otherwise referred to herein as a crotch region 26, extending longitudinally between and interconnecting the front and back regions 22, 24. The pant 20 also defines an inner surface 28 adapted in use (e.g., positioned relative to the other components of the pants 20) to be disposed toward the wearer, and an outer surface 30 opposite the inner surface. The front and back regions 22, 24 are those portions of the pants 20, which when worn, wholly or partially cover or encircle the waist or mid-lower torso of the wearer. The crotch region 26 generally is that portion of the pants 20 which, when worn, is positioned between the legs of the wearer and covers the lower torso and crotch of the wearer. The training pants 20 have a pair of laterally opposite side edges 36 and a pair of longitudinally opposite waist edges, respectively designated front waist edge 38 and back waist edge 39.

The illustrated pants 20 may include a chassis 32, a pair of laterally opposite front side regions 34 extending laterally outward at the front region 22 and a pair of laterally opposite back side regions 134 extending laterally outward at the back region 24.

Referring to FIGS. 1, 6 and 7, the chassis 32 includes an outer cover 40 and a bodyside liner 42 (FIGS. 1 and 7) that may be joined to the outer cover 40 in a superimposed relation therewith by adhesives, ultrasonic bonds, thermal bonds or other conventional techniques. Referring to FIG. 7, the liner 42 may suitably be joined to the outer cover 40 along the perimeter of the chassis 32 to form a front waist seam 62 and a back waist seam 64. As shown in FIG. 7, the liner 42 may suitably be joined to the outer cover 40 to form a pair of side seams 61 in the front region 22 and the back region 24. The liner 42 can be generally adapted, i.e., positioned relative to the other components of the pants 20, to be disposed toward the wearer's skin during wear of the pants. The chassis 32 may further include an absorbent structure 44 particularly shown in FIG. 7 disposed between the outer cover 40 and the bodyside liner 42 for absorbing liquid body exudates exuded by the wearer, and may further include a pair of containment flaps 46 secured to the bodyside liner 42 for inhibiting the lateral flow of body exudates.

With the training pants 20 in the fastened position as partially illustrated in FIG. 1, the front and back side regions 34, 134 can be connected together by a fastening system 80 to define a three-dimensional pants configuration having a waist opening 50 and a pair of leg openings 52. The front and back side regions 34 and 134, upon wearing of the pants 20, thus include the portions of the training pants 20 which are positioned on the hips of the wearer. The waist edges 38 and 39 of the training pants 20 are configured to encircle the waist of the wearer and together define a waist opening 50 of the pants.

The elasticized containment flaps 46 as shown in FIG. 7 define a partially unattached edge which assumes an upright configuration in at least the crotch region 26 of the training pants 20 to form a seal against the wearer's body. The containment flaps 46 can extend longitudinally along the entire length of the chassis 32 or may extend only partially along the length of the chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 may also suitably include a front waist elastic member 54 (FIG. 1), a rear waist elastic member 56, and leg elastic members 58 (FIG. 7), as are known to those skilled in the art. The waist elastic members 54 and 56 can be operatively joined to the outer cover 40 and/or the bodyside liner 42 and can extend over part or all of the waist edges 38, 39. The leg elastic members 58 can be operatively joined to the outer cover 40 and/or the bodyside liner 42 and positioned in the crotch region 26 of the training pants 20.

The waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular aspect, for example, the leg elastic members 58 may include a plurality of dry-spun coalesced multifilament spandex elastomeric threads sold under the trade name LYCRA and available from Invista, Wilmington, Del., U.S.A.

As shown in FIG. 7, the front and back side regions 34 and 134 each have a longitudinal outer edge 68, and a leg end edge 70 disposed toward the longitudinal center of the training pants 20, and waist end edges 72 disposed toward a longitudinal end of the training pants. The leg end edges 70 and the outer edges 68 of the side regions 34 and 134 form part of the pant side edges 36 of the training pants 20. The leg end edges 70 of the absorbent article 20 may be suitably curved and/or angled relative to the lateral direction 49 to provide a better fit around the wearer's legs. However, it is understood that only one of the leg end edges 70 may be curved or angled, such as the leg end edge of the back region 24, or alternatively, neither of the leg end edges may be curved or angled, without departing from the scope of the present invention. The waist end edges 72 are suitably parallel to the transverse axis 49. The waist end edges 72 of the front side regions 34 form part of the front waist edge 38 of the training pants 20, and the waist end edges 72 of the back side regions 134 form part of the back waist edge 39 of the pants. In the figures, the waist end edges 72 and the outer edges 68 are generally horizontal and vertical respectively. It should be understood, however, that in other embodiments, the waist end edges 72 and/or the outer edges 68 may have a curved, slanted or complex arrangement depending upon the particular application.

The side regions may be provided by a non-elastic material or an elastic material capable of stretching at least in a direction generally parallel to the lateral direction 49 of the training pants 20. Suitable elastic materials, as well as one process of incorporating elastic side regions into training pants, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular aspects, the elastic material may include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference to the extent that they are consistent (i.e., not in conflict) herewit. Alternatively, the side region material may include other woven or non-woven materials, such as those described later herein as being suitable for construction of the outer cover 40 and/or the bodyside liner 42; mechanically pre-strained composites; or stretchable but inelastic materials.

The fastening system 80 may include laterally opposite first fastening components 82 adapted for refastenable engagement to corresponding second fastening components 84. In one aspect, a front or outer surface of each of the fastening components 82, 84 includes a plurality of engaging elements. The engaging elements of the first fastening components 82 are adapted to repeatedly engage and disengage corresponding engaging elements of the second fastening components 84 to releasably secure the pants 20 in its three-dimensional configuration.

The fastening components 82, 84 may be any refastenable fasteners suitable for absorbent articles, such as adhesive fasteners, cohesive fasteners, mechanical fasteners, or the like. In particular aspects the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 82 include hook fasteners and the second fastening components 84 include complementary loop fasteners. Alternatively, the first fastening components 82 may include hook fasteners and the second fastening components 84 may be complementary loop fasteners. In another aspect, the fastening components 82, 84 can be interlocking similar surface fasteners, or adhesive and cohesive fastening elements such as an adhesive fastener and an adhesive-receptive landing zone or material; or the like. Although the training pants 20 illustrated in FIG. 1 indicate the back side regions 134 overlapping the front side regions 34 upon connection thereto, which is convenient, the training pants 20 can also be configured so that the front side regions 34 overlap the back side regions 134 when connected. One skilled in the art will recognize that the shape, density and polymer composition of the hooks and loops may be selected to obtain the desired level of engagement between the fastening components 82, 84. Optionally, either one or both of the fastening components 82, 84 may be provided by one of the inner or outer surfaces 28 and 30 of the side regions 34 and 134. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

In addition to the components described above, the absorbent article 20 may further include a surge management layer which may be optionally located adjacent the liner 42 and/or the absorbent structure 44 and attached to various components in the article 20 such as the absorbent structure 44 or the bodyside liner 42 by methods known in the art, such as by using an adhesive. A surge management layer helps to decelerate and diffuse surges or gushes of liquid that may be rapidly introduced into the absorbent structure of the article. Desirably, the surge management layer can rapidly accept and temporarily hold the liquid prior to releasing the liquid into the storage or retention portions of the absorbent structure. Examples of suitable surge management layers are described in U.S. Pat. No. 5,486,166; and U.S. Pat. No. 5,490,846. Other suitable surge management materials are described in U.S. Pat. No. 5,820,973. The entire disclosures of these patents are hereby incorporated by reference herein to the extent they are consistent (i.e., not in conflict) herewith.

In the embodiment shown in FIG. 1, the side regions 34 and 134 of the absorbent article 20 are releasably attachable. It should be understood, however, that in other embodiments, the side regions 34 and 134 may be permanently joined together or may be integral with the chassis 32. For instance, referring to FIG. 2, a perspective view of an alternative embodiment of an absorbent article generally 20 made in accordance with the present invention is shown. Similar reference numerals have been used to indicate similar elements. As shown, in this embodiment, the side regions are integral with the remainder of the article. Alternatively, however, a seam may be present where the sides of the article have been bonded together. The side regions may be bonded together using, for instance, ultrasonic bonding, thermal bonding or an adhesive. In this embodiment, the absorbent article is pulled over the legs when being worn.

Figure 2:
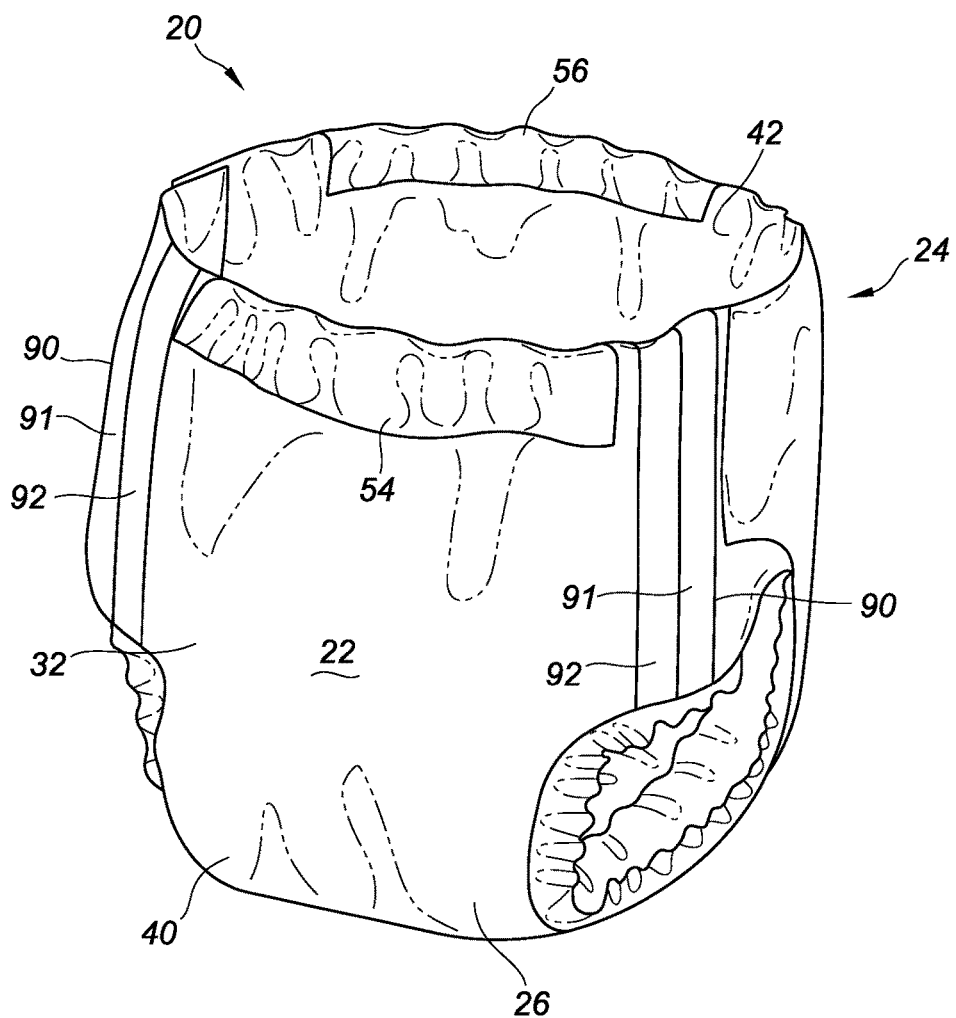
FIG. 2 is a perspective view of an alternative embodiment of an absorbent article made in accordance with the present invention.

As shown in FIGS. 1 and 2, each of the absorbent articles 20 further include a pair of stretchable panels 90 that, in accordance with the present invention, are configured with a first zone 91 and a second zone 92 that upon a certain amount of stretch expose an underlying color and/or pattern in each zone. The stretchable panels 90 are provided on the article to act as a visual stretch indicator. The stretchable panels, for instance, may indicate when the stretchable panels have not been stretched enough, may indicate when the stretchable panels have been stretched an appropriate amount, and/or may indicate when the stretchable panels have been stretched too much. The first zone 91 is configured to expose a first color or pattern upon a first certain amount of stretch. The second zone 92 is configured to expose a second color pattern different than the first color or pattern upon a second certain amount of stretch that is greater than the first certain amount of stretch.

In general, the stretchable panel 90 can be made from any single or multi-layered material that has a first zone 91 that is capable of exposing a first color or pattern upon stretching the first zone to a certain first stretch and a second zone 92 that is capable of exposing a second color or pattern upon stretching the second zone to a certain second stretch that is greater than the certain first stretch. Referring to FIGS. 5A-D, for instance, one particular embodiment of a stretchable panel 90 that may be used in accordance with the present invention is illustrated.

Figure 5A:
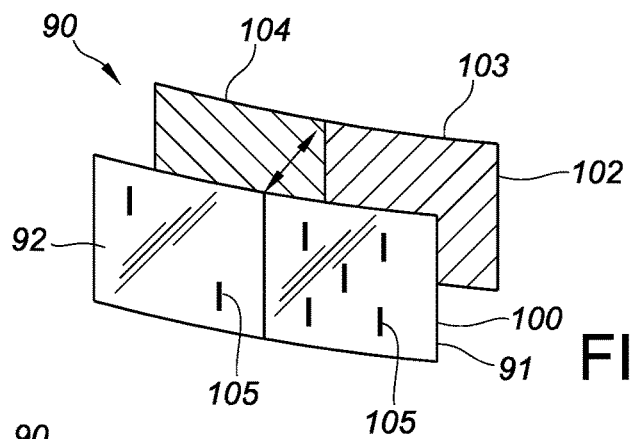
FIGS. 5A, 5B, 5C and 5D are perspective views of an embodiment of a stretchable panel made in accordance with the present invention.
Figure 5B:
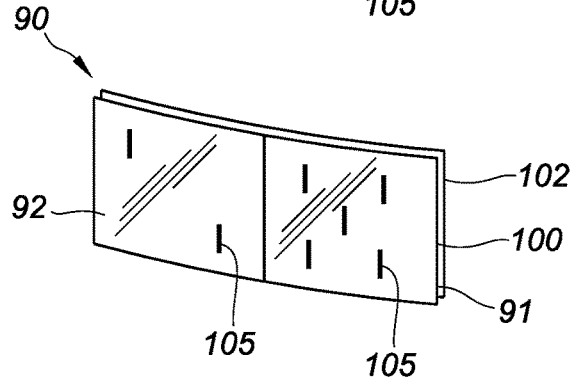

In this embodiment, as shown in FIG. 5A, the stretchable panel 90 includes a stretchable facing layer 100 optionally laminated to an elastic layer 102. The elastic layer 102 may be used if the stretchable panel 90 is intended to be stretchable and elastic. If the stretchable panel 90 is not intended to be elastic, then the elastic layer 102 may be stretchable but not elastic. The stretchable layer 100 and the elastic layer 102 may be films, foams, nonwoven materials, woven materials, knitted materials, or laminates thereof.

Figure 5C:
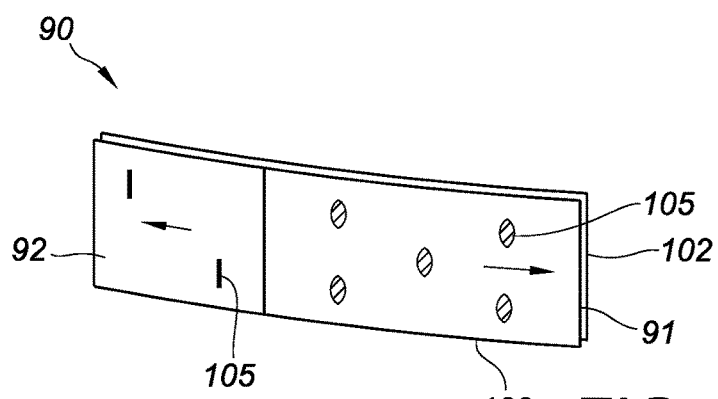
Figure 5D:
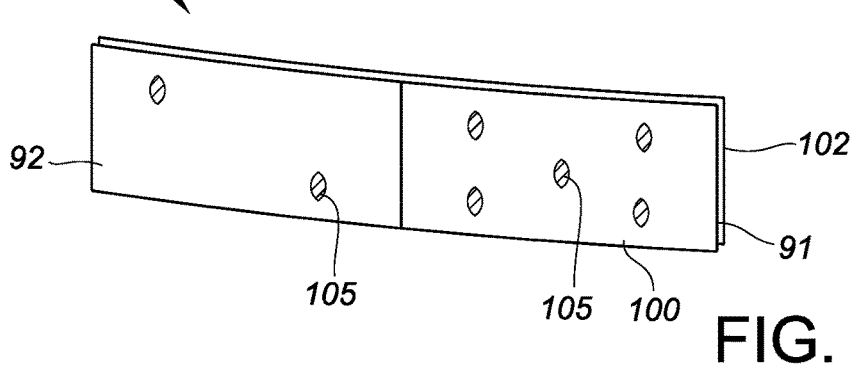

The stretchable layer 100, however, is a material that has a first zone 91 and a second zone 92 that are capable of exposing an underlying color when stretched. In this embodiment, as shown in FIG. 5C, first zone 91 more readily extends under stretching conditions, thus exposing the underlying pattern in the first zone prior to exposing the underlying pattern in the second zone 92. As shown in FIG. 5D, further stretching exposes the underlying pattern in the second zone.

In one embodiment, the stretchable panel 90 as shown in FIGS. 5A-5D may be incorporated into an absorbent article and, when the first zone 91 exposes the underlying first color or pattern, may be used to indicate that the stretchable panel has been stretched by the intended amount. When the second zone 92 exposes the underlying second color or pattern, the stretchable panel has been stretched beyond the intended amount.

The stretch indicating elastic laminate may be composed of a segmented elastic film 102 and at least one facing material 100. The elastic film 102 may have a first segment 103 with a first color or pattern and a second segment 104 having a distinct different second color or pattern. In some embodiments the first segment 103 may be adjacent the second segment 104. The facing material laminated to the segmented film conceals the underlying colors until the laminate is stretched. The facing material has at least one or multiple slits 105 that can be opened or expanded when the material is being stretched. Although not required, the long axis of the slits 105 is easier to open when they are arranged perpendicular or close to perpendicular to the direction of stretching force. The slits 105 are also not restricted to straight cuts; they can be curved or patterned.

When the stretchable panel 90 is stretched the appropriate amount, the slits 105 in the first zone 91 of the facing expand and the first color or pattern is exposed through the slits. When the stretchable panel 90 is stretched beyond the appropriate amount, the slits 105 in the second zone 92 of the facing expand and the second color is exposed through the slits in the second zone. As such, the different colors exposed at different levels of stretch will help the user to adjust the amount of stretch for a better fit.

One approach to controlling the amount of stretch required to expose the underlying color or pattern in a particular zone is to adjust the slit geometries. There are three approaches to control how the slits open to expose each particular colored film at the right amount of stretch. First, increasing the length of the slits will cause the slits to open and expose the underlying pattern or color at a lower amount of stretch. Second, increasing the slit density (slits per unit area) will increase the surface area of the underlying exposed color or pattern. Third, reducing the depth of the slits, i.e., by not cutting the slits all the way through the thickness of the facing material, will increase the amount of stretch required to open the slits and expose the underlying color or pattern.

The second approach to controlling the amount of stretch required to expose the underlying color or pattern in a particular zone is to have different stretch properties of the first and second segments 103, 104 of the elastic film 102 and/or different stretch properties of the first and second zones 91, 92 of the facing material 100. The ratio of the forces required to stretch the first and second segments 103, 104 to 30% extension can be used to determine if the slits 105 in the first zone 91 will open before the slits in the second zone 92. To have the slits 105 in the first zone 91 open prior to the slits in the second zone 92, the ratio of the forces required to stretch the first and second segments to 30% will suitably be between about 1.01 and about 5, more suitably between about 1.5 and 1 bout 3. Alternatively, the ratio of the forces may be measured at 100% extension. The difference in the stretch properties of each segment can be achieved by adjusting composition and/or basis weight and/or applying mechanical treatments such as groove roll stretching, tentering, and other methods as are known to those of ordinary skill in the art.

In other embodiments, the facing material can be a single layer material or a multilayer material, such as, for example, nonwoven/film laminates.

In further embodiments, the facings may be a foam material that breaks apart, splits, or rends upon stretching to expose the underlying color or pattern.

In the embodiments shown in FIGS. 1 and 2, the absorbent article 20 includes a pair of opposing stretchable panels 90 located on the sides of the garment towards the front. It should be understood, however, that the absorbent article may include more or fewer stretchable panels 90. Further, the location and shape of the stretchable panel 90 may change depending upon the particular application. For example, referring to FIG. 3, an alternative embodiment of an absorbent article 120 made in accordance with the present invention is shown. In this embodiment, the absorbent article 120 includes a single stretchable panel 190 located generally in the front region. The stretchable panel 190 includes first zones 191 configured to expose an underlying first color or pattern upon application of a certain first stretch percentage and second zones 192 configured to expose an underlying second color or pattern upon application of a certain second stretch percentage that is greater than the certain first stretch percentage. More particularly, in this embodiment, the stretchable panel 190 comprises an elastic strip in the front region that generally circumscribes the hip circumference of a user.

Figure 3:
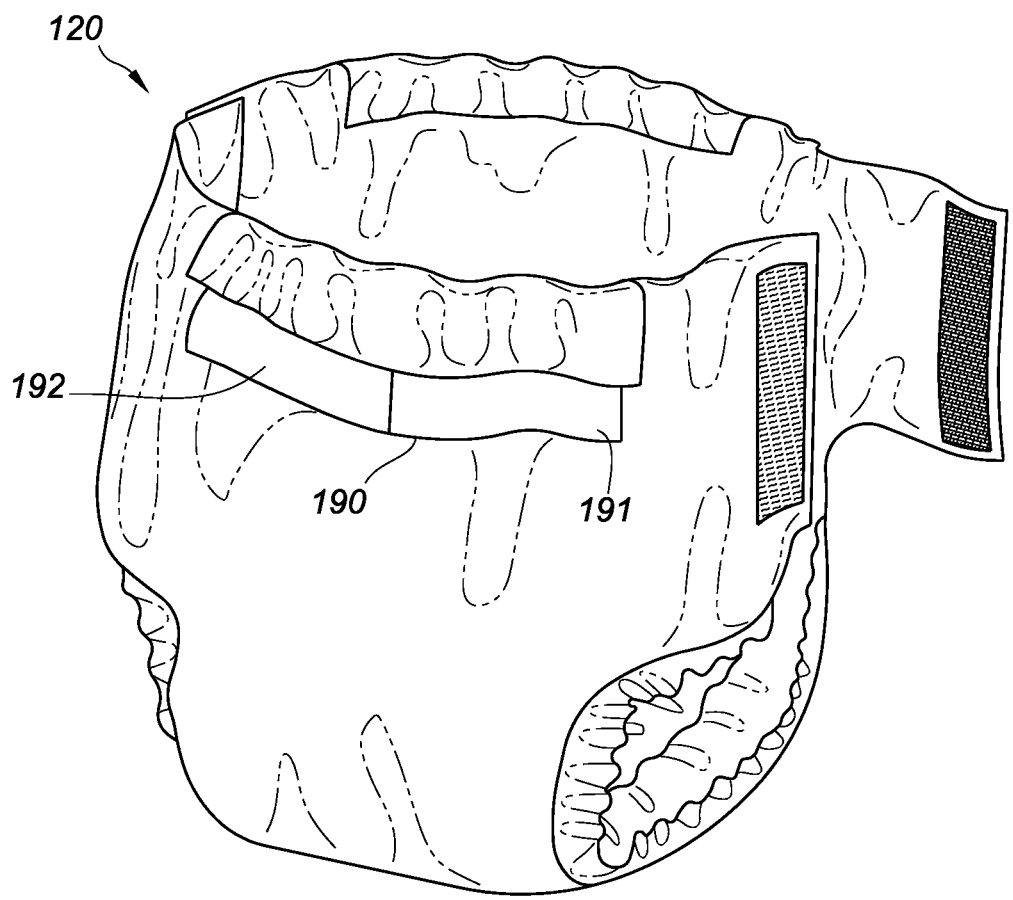
FIG. 3 is a perspective view of still another embodiment of an absorbent article made in accordance with the present invention.

In the embodiment shown in FIGS. 1, 2 and 3, the stretchable panel 90 is generally configured to stretch in the transverse direction. In an alternative embodiment, however, it should be understood that the stretchable panel may also be configured to stretch in the longitudinal direction. In this embodiment, for instance, the stretchable panel may be used as a visual indicator to indicate whether or not the rise of the article is correct and fits properly on the user. In still other embodiments, the stretchable panel may be configured to stretch not only in the longitudinal direction but also in the transverse direction.

Figure 4:
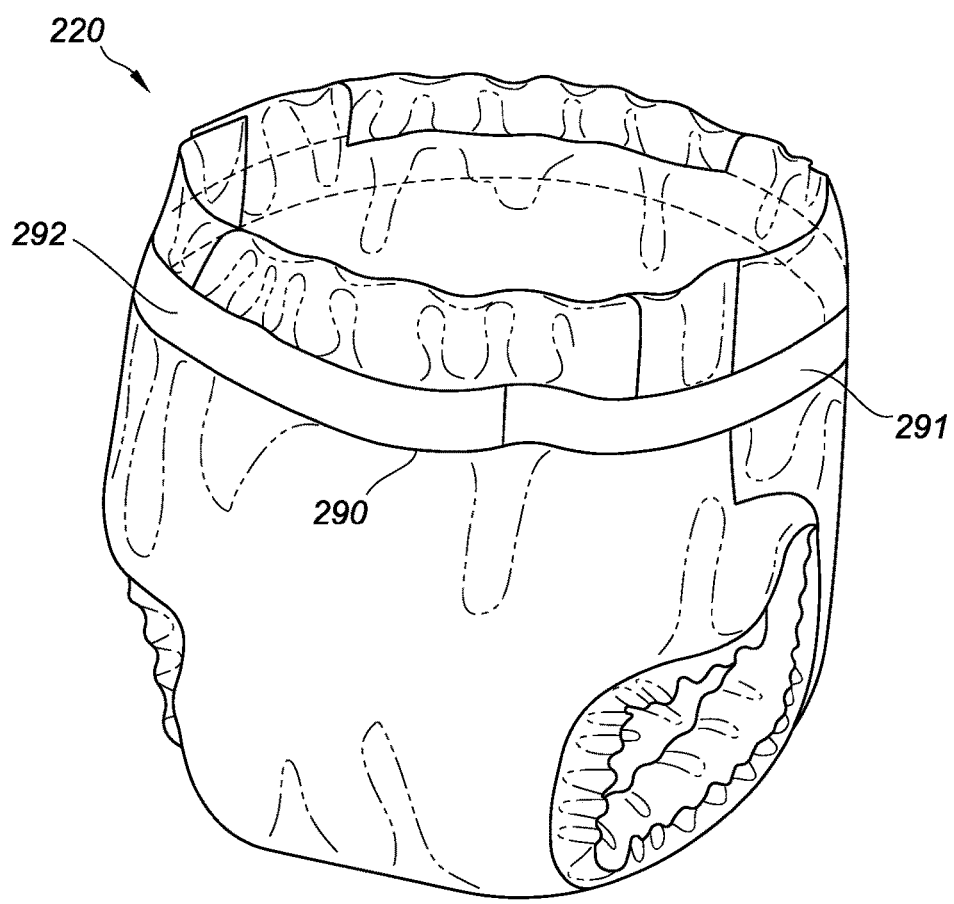
FIG. 4 is a perspective view of still another embodiment of an absorbent article that may be made in accordance with the present invention.

Still another embodiment of an absorbent article 220 made in accordance with the present invention is shown in FIG. 4. As illustrated, the absorbent article 220 includes a stretch indicator panel 290. In this embodiment, the panel 290 includes a band that extends around the entire circumference of the article. The stretchable panel 290 includes first zones 291 configured to expose an underlying first color or pattern upon application of a certain first stretch percentage and second zones 292 configured to expose an underlying second color or pattern upon application of a certain second stretch percentage that is greater than the certain first stretch percentage. The band is located generally at the hip circumference of the user where the article is typically subjected to the most stress and strain.

As described above with reference particularly to FIGS. 1, 6 and 7, the absorbent article 20 includes an outer cover 40, a bodyside liner 42, and an absorbent structure 44. These elements of the absorbent article may be made from conventional materials or can be made from the stretch-indicating stretchable panel itself.

The outer cover 40 may be made from a material that is substantially liquid impermeable, and can be elastic, stretchable or nonstretchable. The outer cover 40 can be a single layer of liquid impermeable material, or may include a multi-layered laminate structure in which at least one of the layers is liquid and permeable. For instance, the outer cover 40 can include a liquid permeable outer layer and a liquid impermeable inner layer that are suitably joined together by a laminate adhesive.

For example, in one embodiment, the liquid permeable outer layer may be a spunbond polypropylene nonwoven web. The spunbond web may have, for instance, a basis weight of from about 15 gsm to about 25 gsm.

The inner layer, on the other hand, can be both liquid and vapor impermeable, or can be liquid impermeable and vapor permeable. The inner layer is suitably manufactured from a thin plastic film, although other flexible liquid impermeable materials may also be used. The inner layer prevents waste material from wetting articles such as bedsheets and clothing, as well as the wearer and caregiver. A suitable liquid impermeable film may be a polyethylene film having a thickness of about 0.2 mm.

A suitable breathable material that may be used as the inner layer is a microporous polymer film or a nonwoven fabric that has been coated or otherwise treated to impart a desired level of liquid impermeability. Other "non-breathable" elastic films that may be used as the inner layer include films made from block copolymers, such as styrene-ethylene-butylene-styrene or styrene-isoprene-styrene block copolymers.

As described above, the absorbent structure is positioned in between the outer cover and a liquid permeable bodyside liner 42. The bodyside liner 42 is suitably compliant, soft feeling, and non-irritating to the wearer's skin. The bodyside liner 42 can be manufactured from a wide variety of web materials, such as synthetic fibers, natural fibers, a combination of natural and synthetic fibers, porous foams, reticulated foams, apertured plastic films, or the like. Various woven and nonwoven fabrics can be used for the bodyside liner 42. For example, the bodyside liner can be made from a meltblown or spunbonded web of polyolefin fibers. The bodyside liner can also be a bonded-carded web composed of natural and/or synthetic fibers.

The bodyside liner 42 may be constructed to be extensible but not elastic. In other embodiments, however, the liner 42 may be configured to be elastic in the longitudinal direction, in the transverse direction, or in both directions.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber. In this particular embodiment, the polypropylene forms the core and the polyethylene forms the sheath of the fiber. Other fiber orientations, however, are possible.

The material used to form the absorbent structure 44, for example, may include cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular embodiment, the absorbent web material is a matrix of cellulosic fluff and superabsorbent hydrogel-forming particles. The cellulosic fluff may comprise a blend of wood pulp fluff. One preferred type of fluff is identified with the trade designation CR 1654, available from US Alliance Pulp Mills of Coosa, Ala., USA, and is a bleached, highly absorbent wood pulp containing primarily soft wood fibers. As a general rule, the superabsorbent material is present in the absorbent web in an amount of from about 0 to about 90 weight percent based on total weight of the web. The web may have a density within the range of about 0.1 to about 0.45 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 15 times its weight in liquid, and suitably is capable of absorbing more than about 25 times its weight in liquid. Suitable superabsorbent materials are readily available from various suppliers. For example, FAVOR SXM 880 superabsorbent is available from Stockhausen, Inc., of Greensboro, N.C., USA; and Drytech 2035 is available from Dow Chemical Company, of Midland, Mich., USA.

In addition to cellulosic fibers and superabsorbent materials, the absorbent pad structures may also contain adhesive elements and/or synthetic fibers that provide stabilization and attachment when appropriately activated. Additives such as adhesives may be of the same or different aspect from the cellulosic fibers; for example, such additives may be fibrous, particulate, or in liquid form; adhesives may possess either a curable or a heat-set property. Such additives can enhance the integrity of the bulk absorbent structure, and alternatively or additionally may provide adherence between facing layers of the folded structure.

The absorbent materials may be formed into a web structure by employing various conventional methods and techniques. For example, the absorbent web may be formed with a dry-forming technique, an airlaying technique, a carding technique, a meltblown or spunbond technique, a wet-forming technique, a foam-forming technique, or the like, as well as combinations thereof. Layered and/or laminated structures may also be suitable. Methods and apparatus for carrying out such techniques are well known in the art.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles or fibers, inorganic absorbent materials, treated polymeric staple fibers and the like. Any of a variety of synthetic polymers may be utilized as the melt-spun component of the coform material. For instance, in some embodiments, thermoplastic polymers can be utilized. Some examples of suitable thermoplastics that can be utilized include polyolefins, such as polyethylene, polypropylene, polybutylene and the like; polyamides; and polyesters. In one embodiment, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference for all purposes.

It is also contemplated that elastomeric absorbent web structures may be used. For example, an elastomeric coform absorbent structure may be used to form the absorbent structure according to the invention. Examples of such elastomeric coform materials are provided in U.S. Pat. No. 5,645,542, incorporated herein in its entirety for all purposes. As another example, a suitable absorbent elastic nonwoven material may include a matrix of thermoplastic elastomeric nonwoven filaments with the matrix including a plurality of absorbent fibers and a super-absorbent material. U.S. Pat. No. 6,362,389 describes such a nonwoven material and is incorporated herein by reference in its entirety for all purposes. Absorbent elastic nonwoven materials are useful in a wide variety of personal care articles where softness and conformability, as well as absorbency and elasticity, are important.

The absorbent web may also be a nonwoven web comprising synthetic fibers. The web may include additional natural fibers and/or superabsorbent material. The web may have a density in the range of about 0.1 to about 0.45 grams per cubic centimeter. The absorbent web can alternatively be a foam material.

Test Method:

Extension Force at 30% and 100%—Stress-Strain testing was done on the samples of 7.62 centimeters wide and 15.24 centimeters long. The sample is placed in the clamps of a Sintech Corp. constant rate of extension tester 2/S with a computer-based data acquisition and frame control system or equivalent with an appropriate load cell so that the peak load falls between 10 and 90 percent of the full-scale load of the load cell (Sintech Corp, of Cary, N.C.). The tests were conducted under ambient conditions. Starting at a 2.54 centimeters gauge length between the sample grips, the sample is elongated at 500 mm/minute to 100% elongation. The data points are recorded and plotted in grams force on the Y axis and % elongation on the X axis. The extension force and energy of each 10% increment elongation from 0% to 100% are recorded.

EXAMPLES

Example 1

Example color segmented films having three segments were produced but only two segments were cut to demonstrate the invention. A Randcastle film die and feed block were configured for making segmented films. The feed block configured for making segmented films with entry ports for two polymers was connected to the center feed port of the die. A first polymer composition (45 wt. % of EXACT™ 5361 available from ExxonMobil Chemical Co., 25 wt. % DOWLEX™ 2047G available from The Dow Chemical Company, 20 wt. % TiO2 concentrate SCC 11692 available from Standridge Color Corp. and 10 wt. % green pigment 10SAM04171 available from Standridge Color Corp.) used to create the center segment of the film. A first extruder (single screw 1.25" Killion extruder) was used to melt the first polymer composition and feed it to one of the feed ports on the feed block. A second polymer composition (80 wt. % of KRATON® MD 6688 available from Kraton Polymers, 10 wt. % TiO2 concentrate SCC 11692 available from Standridge Color Corp. and 10 wt. % red pigment 10SAM04172 available from Standridge Color Corp.) was used for the edge segments. A second extruder (twinscrew Leistritz, 27 mm) was used to melt the second polymer composition and feed it to the second feed port on the feed block. The resultant film had a center segment of the first polymer composition with two edge segments of the second polymer composition. The temperature profile for the first extruder was arranged so that a melt temperature of about 420 F was obtained. The temperature profile for the second extruder was arranged so that a melt temperature of about 200 C was obtained. The die, feedblock and hose temperature settings were 420 F. The winder speed was at 20 fpm. Extension force at both 30% extension and 100% extension was measured as described above for both the green and red films. For the green film, the extension force at 30% extension was 425 grams and the extension force at 100% extension was 620 grams. For the red film, the extension force at 30% extension was 980 grams and the extension force at 100% extension was 1500 grams. The ratio (red:green) of the extension forces at 30% extension was calculated as 2.3. The ratio (red:green) of the extension forces at 100% extension was calculated as 2.4.

The facing material was composed of a white segmented film adhesively laminated to a 26 gsm, 56% necked spunbond. The white segmented film was made using the same set up and process conditions as the color segmented film. The first polymer composition (45 wt. % of EXACT™ 5361 available from ExxonMobil Chemical Co., 25 wt. % DOWLEX™ 2047G available from The Dow Chemical Company, 30 wt. % TiO2 concentrate SCC 11692 available from Standridge Color Corp.) was used for the center segment and the basis weight was about 31 gsm. The second polymer composition (80 wt. % of KRATON® MD 6673 available from Kraton Polymers, 20 wt. % TiO2 concentrate SCC 11692 available from Standridge Color Corp.) was used for the edge segments and the basis weight was about 78 gsm. This white segmented film laminate was slit with a plurality of slit openings that penetrated through the thickness of the laminate. The slits were produced using a table press having steel cutting die to produce a slit pattern with 0.5 inch long slits with 0.25 inch spacing between slits. The columns of slits were spaced at about 0.1875" apart. This slitted white laminate was adhesively laminated to the segmented color film.

Example 2

The segmented colored film was produced same as the Example 1. The facing is a slitted thermoplastic foam material described in U.S. Pat. No. 20060030632A1. The foam was formed using a 2.5/3.5 inch (6.35/8.89 cm) tandem extrusion system and annular die similar to that described in U.S. Pat. No. 6,273,697 to Harfmann and U.S. Pat. No. 6,638,985 to Gehlsen (which are incorporated herein by reference in a manner that is consistent herewith), or equivalents. The primary extruder temperature and screw speed were adjusted to ensure complete polymer and additives melting and mixing and the secondary extruder temperature was adjusted to achieve the desired melt temperature profile to produce foam. The die pressure was achieved by controlling the die gap and extruder screw speeds. The extruded foam was pulled over a cooling mandrel, slit, and wound in a roll.

The thermoplastic foam used polystyrene (STYRON 685D from Dow Chemical Company), thermoplastic elastomer (KRATON DHV, a styrene-ethylene-butylene-styrene block copolymer, from Kraton Polymers), surfactant (CESA-STAT® 3301 from Clariant Corp.) and nucleant (HYDROCEROL® CF-40 T from Clariant Corp. and talc: A27678 from Plastimerics Inc.).

In this example isopentane and carbon dioxide were combined as a physical blowing agent and HYDROCEROL® CF-40-T was used as a chemical blowing agent/nucleant. The raw materials and process parameters are shown in Table 1.

TABLE 1

Raw Material and Process Parameters

| Process Conditions | Units | Sample 1f | Sample 2f |
|---|---|---|---|
| Polystyrene (Dow STYRON ® 685D) | weight % | 47.1 | 45.1 |
| Thermoplastic Elastomer (KRATON DHV) | weight % | 40 | 49 |
| HYDROCEROL ® (Clariant) | weight % | 7.5 | 0 |
| CESA-STAT ® 3301 (Clariant) | weight % | 5.4 | 5.4 |
| Talc A27678 (Plastimerics Inc.) | weight % | 0 | 0.5 |
| Physical blowing agent-iso-pentane | wt. % of polymer | 5.5 | 3.9 |
| Physical blowing agent-carbon dioxide | wt. % of polymer | 0 | 2.2 |
| Primary extruder speed | Rpm | 100 | 100 |
| Secondary extruder speed | Rpm | 12 | 12 |
| Primary extruder last zone temp | F. (C.) | 410 (210) | 410 (210) |
| Secondary extruder last zone temp | F. (C.) | 254 (123) | 241 (116) |
| Die body temperature | F. (C.) | 295 (146) | 295 (146) |
| Melt temperature | F. (C.) | 285 (141) | 280 (138) |
| Die pressure | psi (Kpa) | 931 (6419) | 1497 10322) |
| Pull roll speed | fpm (m/min) | 45 (13.7) | 45 (13.7) |
| Foam throughput (calculated) | lb/hr (kg/hr) | 165 (75) | 178 (81) |

The foam was slit apertured by Rotary Converting in California to produce a slit pattern that the slits were about 0.25 inch long and the slit spacing between slits was about 0.25 inch. The slit foam was adhesively laminated to the segmented color film.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. An extensible sheet material comprising an elastic layer and at least one facing layer, the elastic layer including a first color or pattern and a second color or pattern, the extensible sheet material comprising first and second zones, wherein the second zone is separate from the first zone and the first zone corresponds to the first color or pattern and the second zone corresponds to the second color or pattern, and wherein the first zone exposes the first color or pattern when the extensible sheet material is stretched beyond a first percentage, and further wherein the second zone exposes the second color or pattern when the extensible sheet material is stretched beyond a second percentage greater than the first percentage.

2. The extensible sheet material of claim 1 wherein the ratio of the second zone extension force at 30% extension to the first zone extension force at 30% extension is from about 1.01 to about 5.

3. The extensible sheet material of claim 1 wherein the ratio of the second zone extension force at 100% extension to the first zone extension force at 100% extension is from about 1.01 to about 5.

4. The extensible sheet material of claim 1 wherein the extensible sheet material is a stretch-bonded laminate, neck bonded laminate, or neck stretch bonded laminate.

5. The extensible sheet material of claim 1 wherein the first facing layer zone includes a first plurality of slits through which the first color or pattern is exposed when the extensible sheet material is stretched beyond the first percentage, and wherein the second facing layer zone includes a second plurality of slits through which the second color or pattern is exposed when the extensible sheet material is stretched beyond the second percentage.

6. The extensible sheet material of claim 1 wherein the at least one facing layer comprises a foam or other material without slits wherein the at least one facing layer comprises first and second facing layer zones corresponding to the first and second zones of the extensible sheet material, and wherein the first facing layer zone exposes the first color or pattern when the extensible sheet material is stretched beyond the first percentage, and wherein the second facing layer zone exposes the second color or pattern when the extensible sheet material is stretched beyond the second percentage.

7. The extensible sheet material of claim 1 wherein the first percentage is from about 10 percent to about 50 percent.

8. The extensible sheet material of claim 1 wherein the second percentage is from about 30% to about 150%.

9. The extensible sheet material of claim 5 wherein the first plurality of slits have a first slit length, and wherein the second plurality of slits have a second slit length, and further wherein the first slit length is larger than the second slit length.

10. The extensible sheet material of claim 5 wherein the first plurality of slits have a first slit depth equal to or less than the thickness of the first facing layer zone, and wherein the second plurality of slits have a second slit depth less than the thickness of the second facing layer zone, and further wherein the first slit depth is larger than the second slit depth.

11. The extensible sheet material of claim 5 wherein the first plurality of slits have a first slit density, and wherein the second plurality of slits have a second slit density, and further wherein the first slit density is greater than the second slit density.

12. The extensible sheet material of claim 1, wherein the extensible sheet material is elastic.

13. The extensible sheet material of claim 1, wherein the second color or pattern substantially disappears upon retraction of the extensible sheet material to an extension less than the second percentage.

14. The extensible sheet material of claim 1 wherein the at least one elastic layer comprises first and second elastic layer zones corresponding to the first and second zones of the extensible sheet material, wherein the first elastic layer zone consists of a first elastic composition, and wherein the second elastic layer zone consist of a second elastic composition.

15. The extensible sheet material of claim 14 wherein the first elastic composition comprises predominantly a styrenic block copolymer, and wherein the second elastic composition comprises predominantly an elastic polyolefin.

16. The extensible sheet material of claim 1 wherein the facing layer is selected from the group consisting of woven materials, nonwoven materials, films, foams, and laminates thereof.

17. An absorbent product comprising the extensible sheet material of claim 1.

18. A garment comprising the extensible sheet material of claim 1.

* * * * *